United States Patent [19]

Bell

[11] Patent Number: 5,030,728

[45] Date of Patent: Jul. 9, 1991

[54] CYCLIC COMPOUNDS FOR FORMING COMPLEXES WITH UREA, GUANIDINE AND AMIDINE DERIVATIVES

[75] Inventor: Thomas W. Bell, Miller Place, N.Y.

[73] Assignee: The Research Foundation State University of New York, Albany, N.Y.

[21] Appl. No.: 360,383

[22] Filed: Jun. 2, 1989

Related U.S. Application Data

[63] Continuation-in-part of Ser. No. 215,211, Jul. 5, 1988, abandoned.

[51] Int. Cl.$^5$ ............................................. C07D 471/22
[52] U.S. Cl. ....................................... 546/27; 544/14; 544/63; 544/73; 544/233; 546/26; 546/32; 549/15
[58] Field of Search .............................. 546/26, 27, 32

[56] References Cited

U.S. PATENT DOCUMENTS

| | | | |
|---|---|---|---|
| 4,128,556 | 12/1978 | Cram | 546/26 |
| 4,183,842 | 1/1980 | Ono et al. | 546/32 |
| 4,190,726 | 2/1980 | Schütze et al. | 546/32 |

OTHER PUBLICATIONS

Cram et al., J.A.C.S., vol. 101, 6752-6754 (1979).
Pedersen, J.A.C.S., vol. 89, 2495-2496 (1967).
Kelly et al., J.A.C.S., vol. 109, 6549-6551 (1987).
Bell et al., J.A.C.S., vol. 110, 3673-3674 (1988).
Thummel et al., Inorg. Chemical., 25, 1675-1679 (1986).
Thummel et al., J. Organic Chemical, 50, 2407-2412 (1985).
Bell et al., J. American Chemical Society, 108, 8109-8111 (1986).
Aarts et al., J. American Chemical Society, 108, 5035-5036 (1986).
Bell et al., Tetrahedron Lett., 28, 4817-4820 (1987).
Bell et al., Third Chemical Congress of North America of the American Chemical Society, Jun. 5, 1988.
Bell et al., 196th American Chemical Society National Meeting, Sep. 18, 1988.
Bell et al., 31st National Organic Symposium of the American Society, Jun. 18, 1989.
Bell, T. W., 72nd Canadian Chemical Conference and Exhibition of the Chemical Institute of Canada, Jun. 4, 1989.

*Primary Examiner*—Cecilia Shen
*Attorney, Agent, or Firm*—Hoffmann & Baron

[57] ABSTRACT

A molecule capable of forming stable complexes with urea, guanidine or amidine compounds and the acid addition salts thereof comprises a nucleus of heterocyclic rings.

22 Claims, No Drawings

CYCLIC COMPOUNDS FOR FORMING COMPLEXES WITH UREA, GUANIDINE AND AMIDINE DERIVATIVES

This application is a continuation in part of parent application serial number 215,211, which was filed on July 5, 1988 now abandoned. The entire specification of the parent application is expressly incorporated by reference herein.

Urea, guanidine, amidine, their derivatives and their acid addition salts are present in human bodily fluids, such as serum and urine, where they serve as indications of various disorders. For example, the concentration of urea in blood serum, which is normally expressed as "blood urea nitrogen" (BUN), is used as an indication of renal dysfunction, such as uremia, and nitrogen metabolism; see, for example, (Wright, "Maintenance Hemodialysis", G. K. Hall: Boston (1981), Chpt. 1).

Guanidine and its derivatives, such as N-methyl-guanidine, guanidinoacetic acid, guanidinopropionic acid and guanidinosuccinic acid, are also found in bodily fluids. Assays for determining the concentration of guanidine and its derivatives in blood serum, urine and hemodialysate are useful in detecting certain metabolic disorders such as hyperargininemia and argininosuccinic aciduria; (Kobayashi, et al., Anal. Chem., 58, 1380-1383 (1986)). In the present specification, it will be understood that guanidine refers as well to guanidinium ion.

Amidine derivatives such as dibenzamidines are used as antiprotozoal drugs. Pentamidine isethionate is particularly useful in treating Pneumocystis pneumonia in AIDS patients. It is desirable to be able to assay amidine drugs in bodily fluids in order to optimize dosages. It will be understood in the present specification that amidine refers as well to amidinium ion.

Although it is generally desirable to be able selectively to remove urea, guanidine and amidine compounds and their salts from fluids such as bodily fluids, convenient methods are unavailable. In particular, complexing agents selective for these molecules are not known.

Monocyclic and polycyclic molecules such as crown ethers, cryptands, spherands and torands are known for selectively removing metal cations from solution (Bell, et al., *Journal of Inclusion Phenomena* 5 (1987), 149-152; Pedersen, *J. Am. Chem. Soc.* 1967, 89, 2495-2496; Dietrich et al., *Tetrahedron Lett.* 1969, 2885-2885; Cram et al., *J. Am. Chem. Soc.* 1979, 101, 6752-6754)). Complexing agents that are selective for organic molecules are, however, less readily available. Kelly, et al., has disclosed a complexing agent that is selective for uric acid. (J. Am. Chem. Soc., 109, 6549-6551 (1987)). Aarts et al. has disclosed a crown ether receptor that forms a complex with urea that is soluble in chloroform. (Aarts, et al., J. Am. Chem. Soc., 108, 5035-5036, (1986)). The stability of the urea complex disclosed by Aarts, et al., is insufficient, however, to provide the basis for medical diagnoses which require great selectivity and sensitivity.

Therefore, there is a need for complexing agents that selectively form strong complexes with urea, guanidine, amidine, their ions and derivatives. Urea, guanidine, amidine, their ions and derivatives are intended to include urea, thiourea, guanidine, guanidine mono-substituted on one nitrogen atom, guanidine di-substituted on one nitrogen atom, arginine, and amidine compounds and addition salts thereof. The principal objective of the invention is to provide such complexing agents. Further objectives of the present invention are to provide methods for synthesizing such complexing agents in high yield and purity, and the complexes formed with such complexing agents. These and other objectives as will be apparent to those skilled in the art have been met by providing compounds that form stable complexes with urea, guanidine, and amidine compounds as well as their ions and derivatives. The compounds have structures A-G (all structures are shown at the end of the specification for convenience), wherein:

C represents carbon atoms;
$C_1$ represents carbon atoms preferably bonded to acyclic oxygen, nitrogen or sulfur atoms;
A and G independently represent carbon, sulfur, nitrogen or oxygen atoms;
S independently represents carbon or nitrogen atoms;
D and T independently represent nitrogen, oxygen or sulfur atoms;
X independently represents $(A)_m$;
b independently represents 0-6;
d represents 0 or 1;
s independently represents 1-7, preferably 2-7;
$Z_1$ represents $(A)_p$;
$Z_2$ represents $(A)_q$;
m=0-5;
p and q=0-5 except p and q cannot both be 0;
wherein A, D, S, G or T atoms contain sufficient additional bonds to adjacent A, D, S, G or T atoms or to other atoms to lead to stable molecules; and
wherein an A, S and G atom that represents a sulfur, nitrogen or oxygen atom will not be adjacent to an A, D, S, G or T atom that also represents a sulfur, nitrogen or oxygen atom;

In compounds A-G:
A preferably represents carbon or nitrogen and more preferably carbon;
G preferably represents $sp^2$ hybridized nitrogen, oxygen or sulfur, and more preferably $sp^2$ hybridized nitrogen;
S preferably represents carbon;
D preferably represents $sp^2$ hybridized nitrogen;
T preferably represents oxygen;
$C_1$ preferably represents carbon bonded to acyclic oxygen.
b preferably represents 1-3;
d preferably represents 1;
m preferably represents 0-2;
s preferably represents 2-4;
p and q, independently, preferably represent 0-2.

In a more preferred embodiment of compounds A-G:
A represents carbon;
G represents $sp^2$ hybridized nitrogen;
S represents carbon
D represents $sp^2$ hybridized nitrogen;
T represents $sp^2$ hybridized oxygen
$C_1$ is doubly bonded to acyclic oxygen
b represents 2
m represents 1
d represents 1
s represents 3
p and q independently represent 1.

The structures shown above as A-G comprise the nucleus of atoms of the complexing agents of the present invention. Each atom indicated in the structure possesses a sufficient number of bonds either to adjacent atoms or to other atoms not shown in order to form stable compounds. Stable compounds are those with appreciable lifetimes at room temperature, preferably lifetimes more than one month and more preferably more than one year. The critical aspect of the claimed molecules is that they have D or T atoms in the positions shown. The basic molecules of the invention consist of the atoms shown in FIGS. A-G and as many additional hydrogen or other atoms to render the molecule stable. Any other atoms are possible, although they usually are carbon, oxygen, nitrogen, sulfur, phosphorus, fluorine, chlorine, bromine or iodine. These additional atoms may constitute any organic or inorganic moiety. Some suitable inorganic moieties include, for example, halo, a nitrogen oxide such as nitro, a sulfur oxide such as $SO_3H$, amino and the like.

Suitable organic moieties include, for example, alkyl, aryl, alkylaryl, arylalkyl and substituted amino. The alkyl groups may be branched or unbranched, cyclic or acyclic, and are preferably from 1-30 carbon atoms, preferably 2-20 carbon atoms, and more preferably 3-6 carbon atoms. The alkyl group may be fully saturated or may contain one or more multiple bonds. The carbon atoms of the alkyl group may be continuous or may be separated by one or more functional groups, such as an oxygen atom, a keto group, an amino group, an amido group, an oxycarbonyl group, and the like. The alkyl group may also be substituted with one or more aryl groups as disclosed below. Cyclic organic moities may be aromatic or non-aromatic, and may be fused to other rings, such as to any of the rings shown in structures A-G.

The aryl group may, for example, be a phenyl group, which may be unsubstituted or substituted with any of the inorganic or organic groups discussed above. The aryl group may also be a heteroaryl group, containing one or more ring oxygen, nitrogen or sulfur atom; be five, six or seven membered; and be fused to other saturated or unsaturated rings.

The amino group may be substituted by, for example, any alkyl or aryl group discussed above.

Compounds A-G may, in addition, have additional rings fused to those shown in the formulas.

In general, substituents added to compounds A-G are useful in modifying the solubility properties of the complexing agents. For example, non-polar groups such as alkyl groups enhance the solubility of the compounds in non-polar solvents. Alternatively, polar substituents enhance the solubility of the molecules in polar solvents. Some suitable examples of non-polar substituents include, for example, $C_1$-$C_{10}$, preferably $C_2$-$C_8$, and more preferably $C_3$-$C_6$ alkyl such as methyl, ethyl, propyl, isopropyl, n-butyl, s-butyl, and t-butyl. Some suitable examples of polar groups include, for example, hydroxyl and $-SO_3H$.

The substituents may occur anywhere on compounds A-G. Preferably, they do not occur on atoms forming the cavity of the molecules, where they might interfere with the guest urea, guanidine or amidine molecules in complexes of A-G and such guest molecules.

The substituents added to the molecules of the present invention may be rings of atoms, or may form additional rings fused to the nucleus of rings shown in structures A-G.

Some specific examples of molecules encompassed by formulas A-G are shown as compounds IV, V, VI, VII, VIII, VIIIb, IX, IXb, IXc, IXe, IXf, IXg, X, XI, XII and XIII. These molecules form strong complexes with urea and guanidine compounds. Some structures of complexes formed between compounds IV-XIII as listed above and ligands such as urea, guanidine, amidines, their acid addition salts and the derivatives thereof are shown as complexes IVa, IVb, Va, VIa, VIIa, VIIIa, VIIIc, IXa, and IXd.

In such complexes, urea may be thiourea. The urea, guanidine and amidine compounds may be in the form of ions, such as those in their acid addition salts. The acid addition salt may be formed by treating urea, guanidine and amidine with any acid, such as HCl, HBr, $HNO_3$, $H_2SO_4$, p-toluenesulfonic acid, acetic acid, or benzoic acid.

All of the structures shown above as IV-XIII have at least two n-butyl groups attached to pyridine rings. These butyl groups could be replaced by hydrogen atoms or by any other substituent as discussed above. Moreover, either of the n-butyl substituents or their replacement could be moved to any other position on the ring except for the nitrogen atoms that form hydrogen bonds with a hydrogen atom of the urea, guanidine or amidine molecule as shown in complexes IVa-IXd. These nitrogen atoms correspond to D and T in structures A-G.

The butyl groups at the positions shown in structures IV-IX are convenient for inducing solubility in non-polar solvents such as chloroform. As discussed below, such molecules are easily synthesized.

Compounds IV and V are typical examples of compounds of the present invention. They bind both urea, guanidine and amidine compounds and are especially suitable for binding guanidine that is disubstituted on one nitrogen atom or urea. Compounds IV and V are specific examples of structures A and D, respectively.

Compound VI adds a group having a D—H (i.e. N—H, O—H or S—H) bond to the structure of compound V at a position that allows the added hydrogen atom to form a hydrogen bond with the oxygen atom of urea as shown in complex VIa or with the corresponding nitrogen atom of a guanidine compound. Compounds VII and VIII are examples of compound VI wherein the D—H group is an amino or amido group. The R groups in VII and VIII and anywhere else in the specification may be any of the substituents discussed above in regard to substituents on the rings in structures A-G.

Compound VIIIb is similar to compound IV except that a naphthyridine ring system has been fused to one of the terminal cyclohexanone rings. This compound is a specific example of a molecule encompassed by structure C. Compound VIIIb is especially well suited to form complexes with mono-substituted guanidine compounds, such as arginine, guanidinoacetic acid, guanidinopropionic acid, guanidinosuccinic acid, methyl guanidine, and the like, as shown in complex VIIIc. These complexes have five hydrogen bonds, and are very stable.

Compound IX is similar to compound VIIIb, except that both terminal cyclohexanone rings of IV have been converted to naphthyridine rings. This structure is a specific example of structure F. Compound IX is especially suited to form complexes with guanidine as shown in structure IXa.

Compound IXb is similar to compound IX except for the addition to the terminal naphthyridine ring of a dialkylamino group para to the ring nitrogen atom on both sides of the molecule. The ring nitrogen atoms of the terminal rings are so basic in these molecules that it is protonated in neutral aqueous solution as shown in IXc. The protons are well suited to form hydrogen bonds with the oxygen of urea as shown in compound IXd. As shown in compound IXd, compound IXc is capable of forming six hydrogen bonds with urea.

Compound IXe is a specific example of structure G. Guanidine and guanidinium ion are especially stably complexed by compound IXe. Compounds IXf and IXg are specific examples of structures B and E, respectively.

The compounds of the present invention may be used to dissolve urea, guanidine and amidine compounds in solvents in which they are otherwise insoluble. For example, urea, guanidine and amidine compounds and their acid addition salts may be dissolved in chloroform containing compounds encompassed by host compounds A-G. This selective complexing ability of compounds A-G can be used to separate urea, guanidine and amidine compounds and their acid addition salts from other water soluble compounds by contacting a solid mixture or aqueous solution containing urea, guanidine, or amidine compounds or their salts with chloroform containing a receptor molecule according to structures A-G. When D in structures A-G represents $sp^2$ or $sp^3$ hybridized nitrogen, the urea, guanidine or amidine compounds may be extracted from the chloroform solution by washing the chloroform solution with aqueous acid. This method provides a convenient way to purify urea, guanidine and amidine compounds. If receptor molecules A-G contain an alkyl substituent such as butyl, the receptor molecule remains in the chloroform.

In addition, urea, guanidine and amidine compounds and their salts may be extracted from fluids such as bodily fluids. The removal of urea from blood is desirable to correct renal dysfunction, for example, in dialysis. For this purpose, it is convenient to immobilize receptors A-G. Immobilization can be accomplished by binding the receptors to a polymer, such as those used in protein synthesis. For example, polystyrene can be prepared with electrophilic groups such as chloromethyl. If the receptors contain a nucleophilic group, such as amino or hydroxy, they can be bound to the polymer.

It may also be desirable to remove urea, guanidine and amidine compounds and their salts for the purpose of conducting diagnostic assays. As mentioned above, abnormal concentrations of urea and guanidinium compounds in the blood or urine of a patient may indicate certain renal disfunctions. Since the amino acid arginine has a guanidinium group, it can be selectively complexed in the presence of other amino acids.

In addition to the above utilities, the compounds of the invention selectively form complexes with amidines, such as acetamidine, benzamidine and their acid addition salts, i.e. XIIIa and XIIIb, respectively. Dibenzamidines are particularly important compounds, since they are antiprotozoal agents. Pentamidine isethionate (XIIIc) is a particularly important dibenzamidine, since it is effective in treating Pneumocystis carinii pneumonia in AIDS patients. It is desirable to monitor the level of pentamidine isethionate in patients in order to minimize side effects. Pentamidines may be assayed by first removing it from body fluids, such as from blood, through complexation with compounds of the invention and extraction of the complexes into organic solvents, such as chloroform. Compounds IV and V form especially stable complexes with dibenzamidines. Such a complex between oompound IV and pentamidine isethionate is shown in structure IVb.

Methods for determining the concentration of complexes formed by the compounds of the present invention include spectroscopic methods such as, for example, NMR spectroscopy, UV-visible spectroscopy, and fluorescence spectroscopy. For this purpose, it is desirable to have chromophoric substituents that can be detected by UV-visible and fluorescence spectroscopy wherein the electrons of the chromophoric group are conjugated with the electrons of an atom that forms a hydrogen bond to urea or guanidine. Examples of such molecules are shown as compounds X-XIII.

The chromophoric compounds of the present invention bind urea, guanidine and amidine compounds very strongly. When they do, the wavelength of radiation absorbed by the chromophores shift as a result of the conjugation between the chromophores and the atoms forming hydrogen bonds. This shift may be used as the basis of a spectroscopic determination of the concentration of the complex by standard analytical techniques.

In compounds X-XIII, the following chromophoric groups are shown:

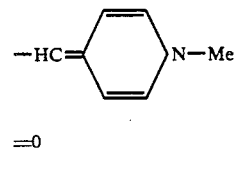

$=\!O$ $=\!C(CN)CO_2CH_3$

Other chromophores known in the art may be used as well In principle, any chromophore that absorbs ultraviolet or visible radiation and that has orbitals conjugated with an orbital on an atom that forms a hydrogen bond in the complex will be suitable.

The compounds of the present invention may be prepared by methods generally known in the prior art. The synthesis of compounds IV, V, IX and IXe will be used for illustration purposes. Modifications of the illustrated reactions will be apparent to those skilled in the art for making other compounds of the invention.

A first key intermediate in the synthesis of compounds IV-IX is 8-n-butyl-2-hydroxytricyclo [$7.3.1.0^{2,7}$] tridecan-13-one, XIV, which may be prepared by treating cyclohexanone with valeraldehyde in a mole ratio of at least 2:1 in the presence of strong base such as potassium hydroxide in ethyl alcohol in accordance with reaction 1. The reaction appears to involve the following sequence: aldol condensation to form 2-pentylidenecyclohexanone, Michael addition of cyclohexanone enolate, and intramolecular aldol condensation of the resulting 1,5-diketone. Many aldol products are formed and the yield of ketoalcohol depends strongly on: (1) reaction temperature; (2) use of a large excess of cyclohexanone; and (3) prolonged addition of the aldehyde. The ease of product isolation is particularly dependent on its crystallinity and solubility. Since ketoalcohol is capable of undergoing a reverse aldol condensation, reactions of XIV may be considered to constitute reactions of the resulting diketone.

A second key intermediate is 9-n-butyl-1,2,3,4,5,6,7,8—octahydroacridine, XV. This intermediate may conveniently be prepared by the well-known reaction of a 1,5-diketone with ammonium, as described by Bell et al., Tetrahedron Lett., 28 4817-4820 (1987). As reported in the Bell et al. article, it has surprisingly been discovered that a cupric salt such as cupric acetate enhances the yield and purity of the product formed. It is especially desirable to conduct this reaction in the presence of at least two equivalents of the cupric salt in the absence of an oxidizing agent such as oxygen. This improved method for converting 1,5-diketones to the corresponding pyridine compound is applicable to any such reaction of a 1,5-diketone with ammonia. The preferred cupric salt is the cupric salt of a carboxylic acid, such as cupric acetate, cupric propionate and cupric butyrate. Cupric acetate is especially preferred. The solvent may conveniently be the corresponding carboxylic acid.

Ketoalcohol XIV may be converted to 9-n-butyl-1,2,3,4,5,6,7,8-octahydroacridine, XV, by treatment with ammonia in accordance with reaction 2. Suitable conditions for this reaction include treatment with ammonium acetate in refluxing acetic acid under nitrogen in the presence of cupric acetate, such as a molar ratio of cupric acetate to XIV of at least about 2.0, and preferably at least about 2.5.

Compound XV may be converted to compound XVII as shown in reactions 3 and 4 by causing the rearrangement of the acetate of the corresponding N-oxide (XVI) of compound XV and isolating the resulting alcohol XVII.

Reaction 3 describes two alternate methods for conversion of a pyridine to its N-oxide: MCPBA and Oxone (potassium hydrogen persulfate). Whereas MCPBA oxidation is relatively standard, the availability of 85% pure MCPBA is limited. Pyridine N-oxides may also be prepared with hydrogen peroxide in acetic acid, but reaction time is variable and removal of acetic acid is inconvenient for large scale preparations. Potassium hydrogen persulfate (Oxone) is an inexpensive alternative to MCPBA in many oxidation reactions. (Trost, et al. Tetrahedron Lett. 1981, 22, 1287-1290; Gallopo, et al., J. Orc. Chem. 1981, 46, 1684-1688; Cicala, et al. ibid. 1982, 47, 2670-2673; Jeyaraman, et al., J. Am. Chem. Soc. 1984, 106, 2462-2463; Murray, et al., J. Org. Chem. 1985, 50, 2847-2853; Davis, et al., ibid. 1988, 53, 2087-2089.)

The oxidation procedure given below in the examples avoids the formation of volatile peroxides, which occurs in ketone-catalyzed N-oxidation of pyridine by persulfate. A 50% excess of Oxone is used, but less oxidant leads to inconveniently long reaction time.

Synthesis of compounds IV-IX from 1,2,3,4,5,6,7,8-octahydroacridines requires oxidative functionalization of the 4-position ($CH_2$ group bonded to the pyridine 2-position). In reaction 4, this is accomplished by "Katada" or "Boekelheid" rearrangement of the N-oxide. Deoxygenation of the acetic anhydride prior to addition results in slightly higher yields.

Compound XVIIa, which is obtained by benzaldehyde condensation from XVII, may be converted to IV as shown in reaction 5. Swern oxidation of XVIIa yields ketone XVIII, which undergoes a Friedlander condensation with a 4-aminopyrimidine-5-carboxaldehyde to afford XIX. (Bredereck et al., Chem. Ber., 100, 3664-3670 (1967)). The pyrimidine ring of XIX undergoes hydrolysis to aminoaldehyde XX, which is condensed with another equivalent of ketone XVIII. The resulting dibenzylidene derivative XXI is then ozonized to diketone IV. This synthesis is effective mainly because two efficient Friedlander condensations are used to form the new 1,8-naphthyridine ring. The synthesis affords diketone IV in 20-35% overall yield.

Additional Friedlander condensation reactions can be employed to convert compound IV into other compounds of the invention. Thus, treatment of IV with two equivalents of 2-methylacrylic acid yields V. Treatment of IV with one equivalent of 2-aminopyridine-3-carboxaldehyde yields VIIIb. A second equivalent yields IX.

Similarly, three additional rings may be added to structure IX, which is shown generically as structure F, to complete the macrocyclic structure of fused rings as shown in structure IXe, which is shown generically as structure G. This type of macrocyclic structure is referred to as a torand. Torand IXe may be prepared, for example, by a double condensation of 2-amino-7-n-butyl-11-oxo-5,6,8,9,10,11hexahydrobenzo[b][1,10]phenanthroline-3-carboxaldehyde, XXI, as shown in reaction 6. Structure XXI may, in turn, be prepared by oxidation of the corresponding benzylidene, XX with CsOH.

Chromophoric groups can be added by methods known in the art. For example, IV may be converted to X by the method of Krasnaya, et al. or of Nair, et al. (Krasnaya, et al. Akad. Nauk, Eng. Trans., 102-107 (1978); Nair, et al. Tetrahedron Lett., 21, 3155-3158 (1980), J. Org. Chem., 46, 4759-4765 (1981)).

Alternatively, torand IXe may be prepared by ozonolysis of benzylideneketone XVIIa, which gives an octahydroacridinediketone that may be condensed with two equivalents of 4-aminopyrimidine-5-carboxaldehyde. The terminal pyrimidine rings of the resulting seven-ring intermediate are then hydrolyzed to give a bis(aminoaldehyde) analogous to the mono(aminoaldehyde) XX. Friedlander condensation of this intermediate with diketone IV gives a 15-ring macrocylcle containing three pyridines and three 1,8-naphthyridines.

The 24-membered ring cavity of this macrocycle has a nearly ideal shape and size to form a stable, lipophilic complex having six hydrogen bonds with guanidinium.

EXAMPLES

A.

8-n-Butyl-2-hydroxytricyclo[7.3.1.0$^{2,7}$]tricedan-13-one.(XIV)

A 2-L, three necked flask is equipped with a magnetic stirring bar, a thermometer, a 500-mL pressure equalizing dropping funnel, and a reflux condenser equipped with a nitrogen gas inlet tube, which is attached to a mineral oil bubbler. The flask is charged with 1.0 L (947 g, 9.65 mol) of cyclohexane (Note 1) then flushed with nitrogen. The cyclohexane is heated to 70-75° C. under nitrogen, then a solution of 9.0 g (0.14 mol) of potassium hydroxide (Note 2) in 85 mL of absolute ethanol is added in one portion, followed by a solution of 150 mL (122 g, 1.4 mol) of valeraldehyde (Note 3) in 140 mL of absolute ethanol, added dropwise over a period of 8 hrs. The stirred reaction mixture is maintained at 70-75° C. throughout the addition period and for 11-14 hrs. after the addition is complete. The reaction flask is then immersed in an ice bath and crystallization is initiated by scratching with a glass rod or by adding seed crystals. Crystallization is complete within four hours at 0° C. and the colorless product is collected by vacuum filtration and washed with cooled ether (200 mL) (Note 4). The product is recrystallized from methanol, washed with water and dried (1 mm, 60° C.) to give 146 g (40%)

of 8-n-butyl-2-hydroxytricyclo[7.3.1.0$^{2,7}$] tridecan-13-one, mp 140–141° C. (Note 5).

B. 9-n-Butyl-1,2,3,4,5,6,7,8-octahydroacridine. (XV)

A 500 mL, one-necked flask equipped with a magnetic stirring bar, a Claisen adapter, and a reflux condenser equipped with a nitrogen inlet attached to a bubble (Note 6) is charged with 17.0 g (0.22 mol) of ammonium acetate, 82 g (0.41 mol) of cupric acetate monohydrate and 200 mL of glacial acetic acid, then flushed with nitrogen. The mixture is stirred and heated at reflux under a static atmosphere of nitrogen for 15 min., then the resulting solution is cooled slightly as 53 g (0.20 mol) of 8-n-butyl-2-hydroxytricyclo[7.3.1.0$^{2,7}$]-tridecan-13-one is added in several portions. The blue-green reaction mixture is stirred and heated at reflux under nitrogen for 3 hrs., then the reaction flask is cooled in an ice bath for 2–3 hours. Precipitated cuprous acetate is removed by vacuum filtration using a fitted glass funnel (medium or coarse porosity) and washed with 100 mL of acetic acid. The combined filtrates are diluted with 500 mL of water, cooled in ice and carefully neutralized by slow addition of aqueous sodium hydroxide (Note 7). The resulting cloudy mixture is transferred to a separatory funnel and extracted with ether (400 mL, then 2× 200 mL). The combined ether extracts are washed with 140 mL of 3% aqueous sodium hydroxide and 70 mL of saturated aqueous sodium chloride, then dried using anhydrous magnesium sulfate with 1 g of decolorizing charcoal (Norit). The solids are removed by filtration and washed with at least 200 ml of ether. The combined filtrates are concentrated to minimum volume using a rotary evaporator and residual solvent is removed under vacuum (1mm). The product is obtained as a beige crystalline solid, mp 35–37° C., 47 g (97%) (Note 8).

C. 9-n-Butyl-1,2,3,4,5,6,7,8-octahydroacridine-N-oxide (XVI)

Method 1:

Into a 2L round-bottomed flask equipped with a magnetic stirrer and a reflux condenser fitted with a nitrogen inlet are placed 38.0 g (0.16 mol) of 9-n-butyl-1,2,3,4,5, 6,7,8-octahydroacridine, 72.0 g (0.12 mol) of Oxone (Note 9), 28.5 g (0.34 mol) of NaHCO$_3$, 790 mL of methanol and 240 mL of water. The resulting suspension is stirred at 45–50° C. in an atmosphere of nitrogen for 24 hrs. (Note 10). The cooled reaction mixture is vacuum filtered, washing the residual salts with methanol (2×50 mL). The methanol is removed from the combined filtrates by means of a rotary evaporator and the resulting mixture is extracted with methylene chloride ( 3× 100 mL). The combined extracts are washed with water (2×50 mL), dried using anhydrous magnesium sulfate and concentrated to dryness by means of a rotary evaporator. Residual solvent is removed at 0.1 mm, yielding 39 g (96%) of 9-n-butyl-1,2,3,4,5,6,7,8-octahydroacridine-N-oxide as a pale yellow solid, mp 89–92° C. (Note 11).

Method 2:

Into a 1 L round-bottomed flask equipped with a magnetic stirrer, a reflux condenser and a 250 ml addition funnel are placed 56.3 g (0.26 mol) of m-chloroperoxybenzoic acid (Note 12) and 350 mL of methylene chloride. The resulting suspension is stirred as a solution of 38.0 g (0.16 mol) of 9-n-butyl-1,2,3,4,5,6,7,8-octahydroacridine in 120 mL of methylene chloride is added rapidly. When the reaction mixture ceases to boil gently from the heat of reaction, the reaction flask is warmed to extend the reflux period to a total of 2.5 hrs. (Note 10). The reaction mixture is cooled to room temperature, extracted with 0.5 M aqueous sodium hydroxide (4× 450 mL), dried using anhydrous sodium sulfate and concentrated under reduced pressure using a rotary evaporator. Residual solvent is removed at 0.1 mm, yielding 40 g (99%) of 9-n-butyl-1,2,3,4,5,6,7,8-octahydroacridine-N-oxide as a yellow crystalline solid, mp 96–100° C.

D. 5-Benzylidene-9-n-butyl-1,2,3,4,5,6,7,8-octahydroaoridine-4-ol

HBr Salt. (XVIIa (HBr))

A mixture of 40 g of crude 9-n-butyl-1,2,3,4,5,6,7,8-octahydroacridine N-oxide and 300 mL of degassed acetic anhydride is heated under nitrogen at 100–110° C. for 2 hours, then 100 mL (104 g, 1 mol) of benzaldehyde is added. The reaction mixture is heated under reflux for 18 hours, then 300 mL of distillate is collected by simple distillation under vacuum (25–35 mm). A solution of the residual dark oil in 150 mL of methylene chloride is washed with 2×100 mL of 2 M aq. NaOH, then evaporated to dryness. A mixture of the residue, 150 mL of 48% aq. HBr and 800 mL of water is distilled at atmospheric pressure until 600 mL of distillate is collected. The port liquid is cooled with ice for 2 hours, then the aqueous layer is decanted. The residual dark, viscous oil is taken up in about 200 mL of acetone and the resulting mixture is stored at 0–5° C. for several hours. The crude product is collected by vacuum filtration and recrystallized from acetone/ethyl acetate, yielding 34.8 g (50.1%) of yellow crystalline product, m.p. 183.5–184.5° C.

E. 5-Benzylidene-9-n-butyl-2,3,5,6,7,8-hexadro-4(1H)-acridinone.

(XVIII)

A mixture of 21.4 g of 5-benzylidene-9-butyl-1,2,3,4,5,6,7,8-octahydroacridin-4-ol HBr salt, 100 mL of methylene chloride and 100 mL of 1 M aq. NaOH is shaken in a separator funnel until all solids have dissolved in the methylene chloride layer. The organic layer is collected and dried with anhydrous Na$_2$SO$_4$. After removing solvent by rotary evaporator and high vacuum (0.1 mm), the residue is dissolved in 140 mL of DMSO. Acetic anhydride (90mL) is added to the DMSO solution and the reaction mixture is stirred for 6 hours. Water (600 mL) is added and the mixture is extracted with 3×200 ml of ether. The combined ether layers are washed with 3×100 mL of 1 M NaOH solution and dried over anhydrous Na$_2$SO$_4$. Solvent is removed under vacuum and the residue is recrystallized from ethylacetate/hexane to give 12.5 g (72%) of crystalline product, m.p. 119.5–112.5° C.

F. 1,16-Dibenzylidene-5.12-di-n-butyl-1,2,3,4,6,7,10, 11,13,14,15,16-dodecahydrodibenzo [b.g][1,10] phenanthrolino

[2,3-[1,10]phenanthroline. (XXI)

To a refluxing solution of 3.47 g of 5-benzylidene-9-n-butyl-2,3,5,6,7,8-hexahydro-4(1H)-acridinone and 1.24 g of 4-aminopyrimidine-5-carboxaldehyde in 800 mL of methanol is added 0.1 mL of 15% methanolic KOH. The mixture is refluxed for 24 hours and 2.58 g precipitate is collected by vacuum filtration after cooling. The solution of this intermediate in 500 mL of 2M HCl is heated under reflux for 3 hours. The reaction mixture is cooled and filtered, yielding 2.53 g of orange solid, which is then mixed with 2.08 g of 5-benzylidene-9-n-butyl-2,3,5,6,7,8-hexahdro-4-(1H)-acridi none and 250 mL of methanol and heated to reflux, then 4 mL of 15% methanolic KOH is added and the refluxing is continued for 24 hours. Yellow solid product is obtained by vacuum filtration, 3.82 g (52.2%), m.p. 282.C (dec.).

G.
5,12-Di-n-butyl-2,3,4,6,7,10,11,13,14,15-decahydrodibenzo

[b,c,] [1,10] phenanthrolino [2,3-b] [1,10] phenanthroline-1,16-dione.

(IV)

1,16-Dibenzylidene-5,12-di-n-butyl-1,2,3,4,6,7,10,11, 13,14,15,16-dodecahydrodibenzo [b,g] [1,10] phenanthrolino [2,3-b] [1,10] phenanthroline (0.3 g) is dissolved in a mixture of 110 mL of methylene chloride and 40 mL of methanol. At $-78°$ C. ozone is bubbled through the orangish-yellow solution until the color of the solution is changed to pale greenish-yellow. The solution is then purged with $N_2$ for 5 minutes. Dimethyl sulfide (0.5 mL) is added and the reaction mixture is warmed to room temperature. The solvents are removed by rotary evaporation. The residue is washed with 100 ML of ether, yielding 0.24 g of crude product (100%), which is recrystallized with a mixture of methylene chloride and isopropanol. Slow evaporation of methyl chloride yields 0.11 g (46%) of crystalline product, m.p. 296–300° C. (dec.).

H.
7,14-Di-n-butyl-5,6,8,9,12,13,15,16-octahydrodicuino [8,7-b,g]

[1,10]-phenanthrolino [2,3-b] [1,10] phenanthroline. (V)

A solution of 5 mmol of 5,12-di-n-butyl-2,3,4,6,7,10,11,13, 14,15-decahydrodibenzo [b,g] [1,10] phenanthrolino [2,3-b] [1,10] phenanthroline-1,16 dione, 12 mmol of o-allylhydroxylamine hydrochloride, 1 g of anhydrous sodium acetate, 1.2 g of anhydrous sodium carbonate and 30 ml of ethanol is stirred under reflux for 6 hours. The ethanol is evaporated and the residue is extracted with chloroform. The combined chloroform extracts are washed with water, dried over $MgSO_4$ and evaporated to obtain the oxime intermediate, which is purified by recrystallization or chromatography. The intermediate is heated at 180–185° C. in a sealed glass tube for 48 hours. The cooled tube is opened and the contents are dissolved in chloroform. The chloroform solution is washed with water, dried over $Na_2SO_4$ and evaporated. The crude product is purified by recrystallization or chromatography.

I.
8,15-Di-n-butyl-6,7,9,10,13,14,16,17-octahydrodi(benzo[b]

[1,8]naphthyridino)[9,8-b,g][1,10]-phenant hrolino[2,3-b]

[1,10]phenanthroline (IX)

A suspension of 117 mg (0.2 mmol) of diketone (IV) and 60 mg (0.49 mmol) of 2-aminopyridine-3-carboxaldehyde is stirred under $N_2$ and heated under reflux as 0.01 mL of 15% methanolic KOH solution is added. The reaction mixture is heated under reflux an additional 20 hr., then cooled to room temperature and filtered. The precipitate is recrystallized by slow evaporation of a solution in dichloromethane/ethanol to yield 67.2 mg (44%) of crystalline product.

J.
2-Amino-7-n-butyl-11-oxo-5,6,8,9,10,11-hexahydrobenzo

[b][1,10]phenanthroline-3-carboxaldehyde (XXI)

A solution of 0.46 g (1 mmol) of 2-amino-11-benzylidene-7-n-butyl-5,6,8,9,10,11-hexahydrobenzo [b][1,10]phenanthroline-3-carboxaldehyde HCl salt (XX) in 40 mL of dichloromethane and 20 mL of methanol is stirred at approximately $-78°$ C. and ozone is bubbled through the orangish-yellow solution. When the color of the reaction mixture changes to pale greenish-yellow, the solution is immediately purged by bubbling in $N_2$ for 5 minutes. Dimethylsulfide (1.0 mL) is added and the reaction mixture is allowed to warm to room temperature. The solvents are removed by rotary evaporation and the residue is triturated with 100 mL of ether, yielding 0.39g (100%) of product.

K. Torand IXe

A solution of 0.39 g of 2-amino-7-n-butyl-11-oxo-5,6,8,9,10,11-hexahydrobenzo-[b][1,10]-phenanth roline-3-carboxaldehyde(XXI) in 50 mL of ethanol is added by syringe pump over 2 hr. to a rapidly stirred solution of 0.15 mL of 50% aq. CsOH in 50 mL of ethanol, which is heated at reflux under $N_2$. The reaction mixture is heated under reflux for an additional 22 hr., then cooled to room temperature. The solvent is removed by rotary evaporation and 5 ml of $CHCL_3$ is added to the residue. The mixture is cooled overnight in a refrigerator, then filtered to collect 0.20 g (55%) of torand IXe, which may be further purified by recrystallization from 95% a8. ethanol.

L. urea complex of Diketone IV (Compound IVa)

Method 1:

A solution of 22.2 mg (0.04 mmol) of compound IV in 2 ml of $CHCl_3$ or CDCl is shaken in a tightly stoppered centrifuge tube with a solution of 0.24 g (4 mmol) of urea in 2 ml of water or $D_2O$ for 1–16 hours at room temperature. At least 0.95 equivalents of urea are extracted into the organic layer, as determined by NMR, gravimetric or colorimetric analysis.

Method 2:

A solution of 118 mg (0.20 mmol) of compound IV in 10 ml of methylene chloride is mixed with a solution of 12 mg (0.20 mmol) of urea in 5 ml of methanol. Removal of solvents by rotary evaporation and recrystallization from ethanol gave the 1:1 complex as a fine yellow powder.

M. Complex of Compound IX with Guanidinium Chloride (Compound

IXa).

A suspension of 585 mg (1 mmol) of diketone (IV) and 300mg (2.5 mmol) of 2-aminopyridine-3-carboxaldehyde is stirred under $N_2$ and heated under reflux as 0.05 mL of 15% methanolic KOH solution is added.

The reaction mixture is heated under reflux an additional 48 hr., then cooled to room temperature. Guanidinium chloride (600 mg, 6.3 mmol) is added and the mixture is heated under reflux for one hr.,m then cooled to room temperature. Vacuum filtration gives 642 mg (75%) of yellow solid, proven to be 1: 1 complex IXa by $^1$H NMR spectroscopy of a solution in $CDCl_3/DMSO$-$d_6$.

N. Complex of Diketone (IV) with Pentamidine Isethionate

A suspension of 5.8 mg (0.01 mmol) of compound IV in 1 mL of $CDCl_3$ is shaken in a tightly stoppered centrifuge tube with 1 mL of 0.01 M aq. pentamidine isethionate for 1 hr. at room temperature. The layers are separated and the $CDCl_3$ layer is observed to contain a 2: 1 ratio of compound IV and pentamidine isethionate, according to $^1$H NMR spectroscopy.

NOTES FOR EXAMPLES

1. Cyclohexane (99%) was obtained from Lancaster Synthesis and was used without purification.

2. Potassium hydroxide (86.6%) was certified grade from Fisher Scientific.

3. Valeraldehyde (bp 98–100° C.) was obtained from Aldrich Chemical Company, distilled under a static atmosphere of nitrogen and stored at −26° C.

4. Additional product may be isolated from the combined filtrates, which are concentrated to approximately 200 mL using a rotary evaporator. The white solid is collected by vacuum filtration and washed with water (2×200 mL) and cold ether (200 mL), then recrystallized from methanol and dried to give 84 g (23%), mp 140–141° C.

5. The product has the following spectroscopic properties: $^1$H NMR ($CDCl_3$) δ: 0.88 (t, 3 H, $CH_3$), 1.1–2.3 (m, 23 H, $CH_2$, CH), 2.4 (m,1 H, $CH_2$), 2.6 (s, 1 H, OH); IR (KBr)$cm^{-1}$: 3400(s), 2920(s), 2850(s), 1705(s), 1450(m), 1410(m), 1350(m), 1290(m), 1270(m), 1210(m), 1145(m), 970(m), 935(m); mass spectrum, m/z (relative abundance, 70 eV): 264 (M+, 10%), 167 (85%), 166 (100%). A second recrystallization from methanol gave a sample for microanalysis. Anal. Calcd for $C_{17}H_{28}O_2$: C, 77.22; H, 10.67. Found: C, 77.34: H, 10.51 %.

6. The condenser is fitted to the side-arm of the Claisen adapter.

7. Approximately 470 mL of 33.3% (w/w) aqueous sodium hydroxide was required to reach a final pH of 8-9. Lower pH leads to extraction of acetic acid, whereas higher pH (10) causes the formation of a white precipitate that makes phase separation difficult during extraction.

8. The product has the following spectroscopic properties: $^1$HNMR ($CDCl_3$)δ: 0.96 (t, J=6 Hz, 3H, $CH_3$), 1.3–1.5 (m, 4 H $CH_2$—/$CH_2$—/ $CH_3$), 1.7–1.9 (M, 8 H, H2, H3, H6, H7), 2.5–2. 9 (m, 10 H, Ar—$CH_2$); IR (neat) $cm^{-1}$: 2930(s), 2860(s) 1435(m), 1410(m), 1240(w); mass spectrum, m/z (relative abundance, 70 eV): 243 ($M^{30}$, 51%), 228 (6%), 214 (16%), 201 (64%), 200 (56%), 186 (100%). An analytical sample was obtained by bulb-to-bulb distillation (1 mm). Anal. Calcd for $C_{17}H_{25}N$: C, 83.89; H, 10.35; N 5.75. Found: C. 83.58; 10.07; N, 5.40 %.

9. Oxone, the DuPont trade name for potassium peroxymonosulfate, has the composition $2KHSO_5$ $KHSO_4$ $K_2SO_4$ and was supplied by Aldrich Chemical Company.

10. Oxidation may be monitored by thin-layer chromatography (alumina, ethyl acetate; N-oxide $R_f$ 0.2–0.3). Trace amounts of unreacted 9-n-butyl-1,2,3,4,5,6,7,8-octahydroacridine ($R_f$ 0.7) do not effect subsequent product yields, but reaction time may be extended to effect complete conversion.

11. The crude product is sufficiently pure to be used directly in part D, but may be purified by recrystallization from ethyl acetate/hexanes, mp 98–99° C.; $^1$HNMR ($CDCl_3$)δ: 0.96 (t, J=6 Hz, 3 H, $CH_3$), 1.41 (m, 4 H, $CH_2$—$CH_2$—$CH_3$), 1.7–1.9 (m, 8 H, H2, H3, H6, H7), 2.50 (m, 2 H, 9-$CH_2$), 2.68 (m, 4 H, H11, H8), 2.96 (m, 4 H, H4, H5).

12. MCPBA was technical grade (80–85%) supplied by Aldrich Chemical Co. or Lancaster Synthesis Ltd.

STRUCTURES

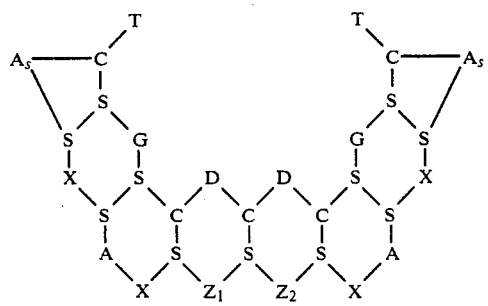

A

-continued
STRUCTURES
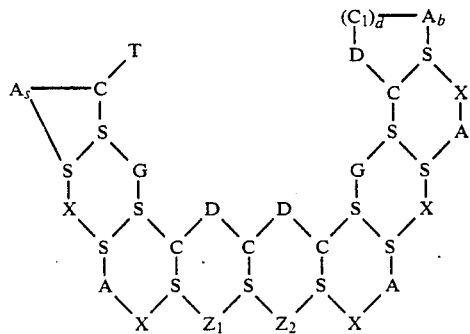 B
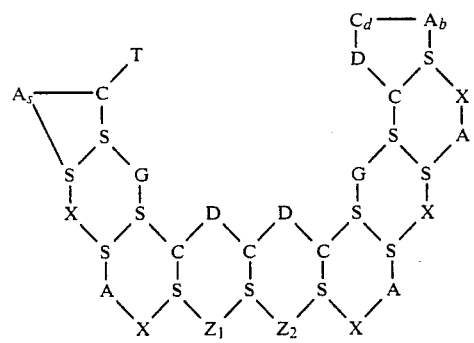 C
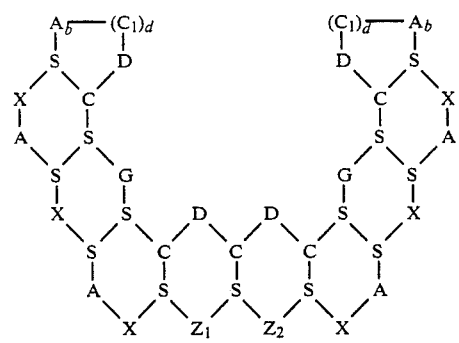 D
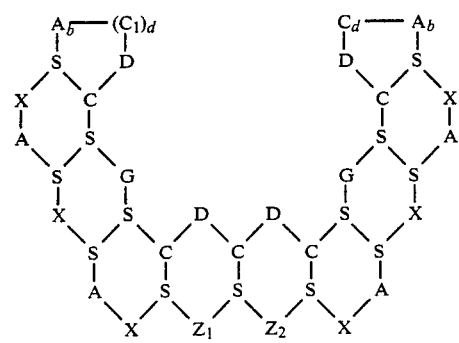 E

-continued
STRUCTURES
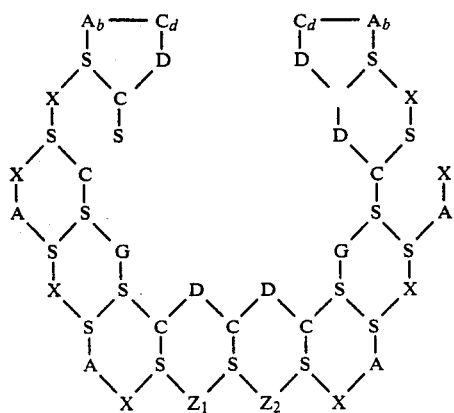   F
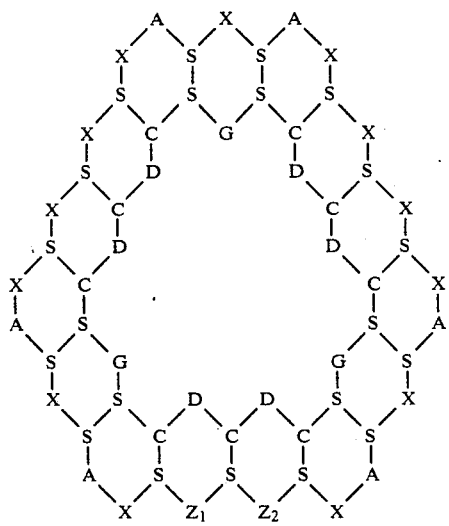   G
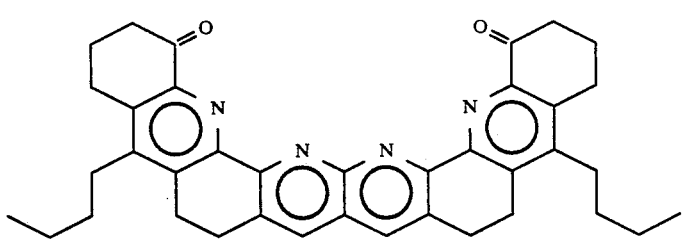   IV
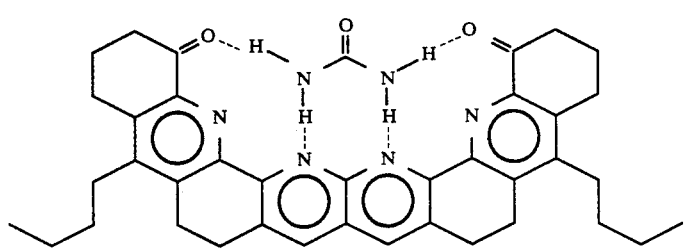   IVa -continued
STRUCTURES
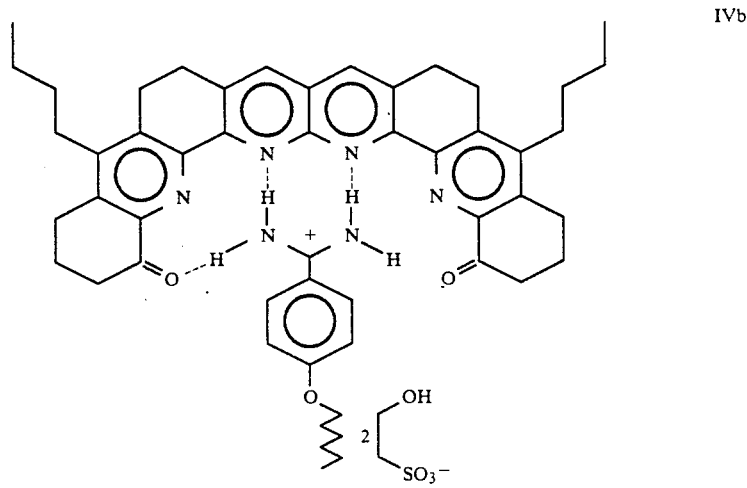
IVb
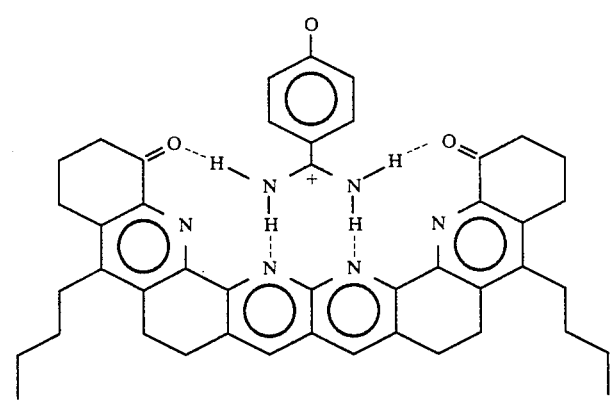
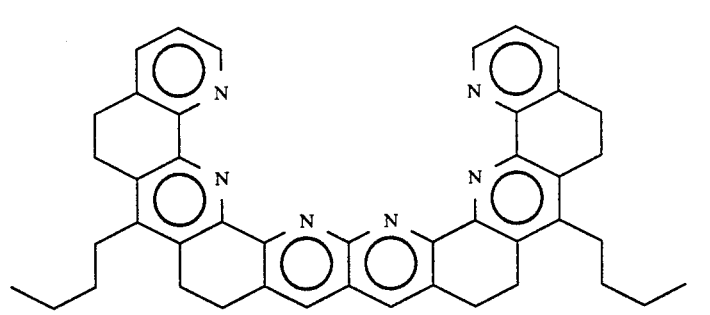
V
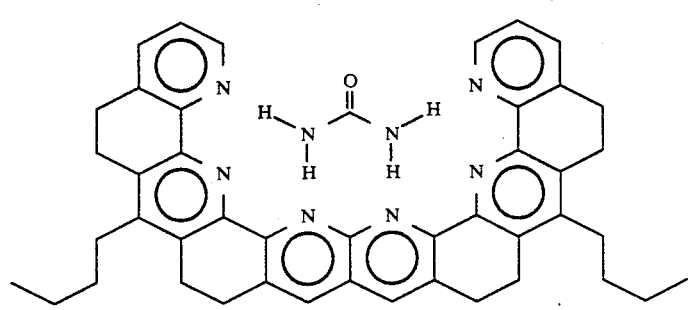
Va -continued
STRUCTURES
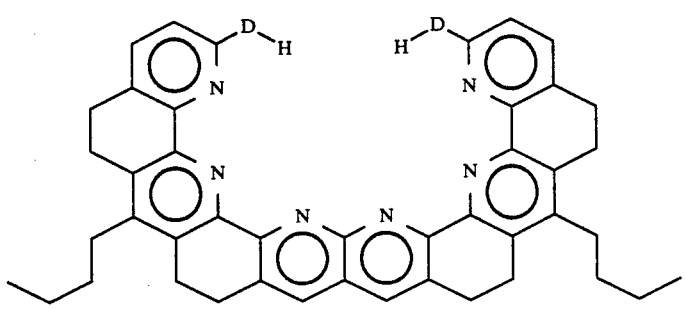
VI
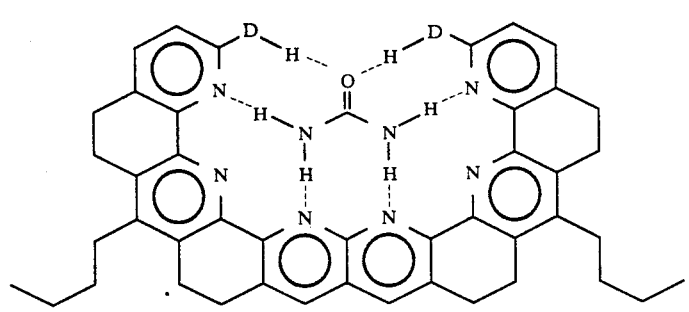
VIa
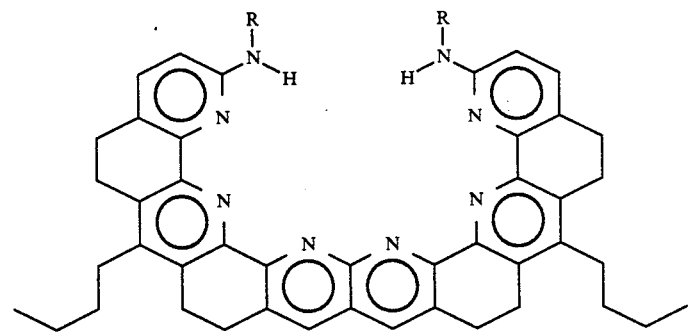
VII  R = H
VIII  R = COCH₃
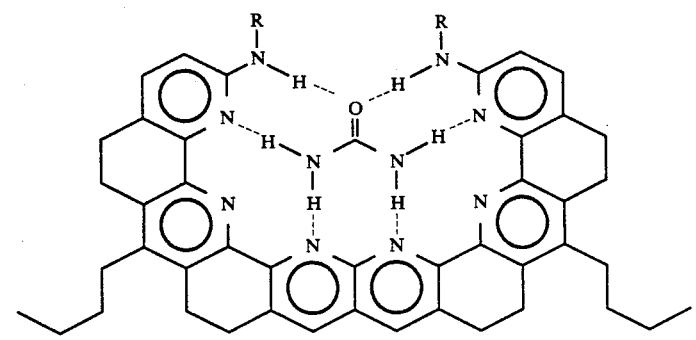
VIIa  R = H
VIIIa  R = COCH₃

-continued
STRUCTURES
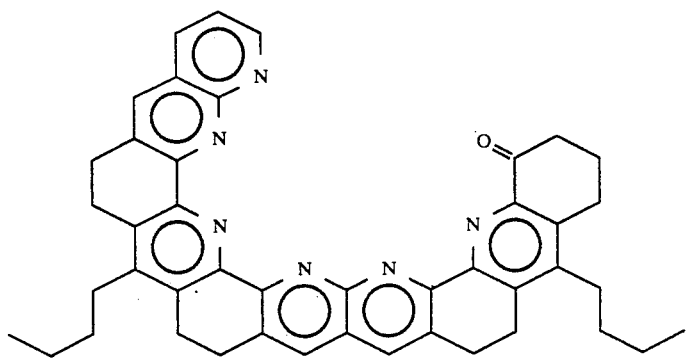
VIIIb
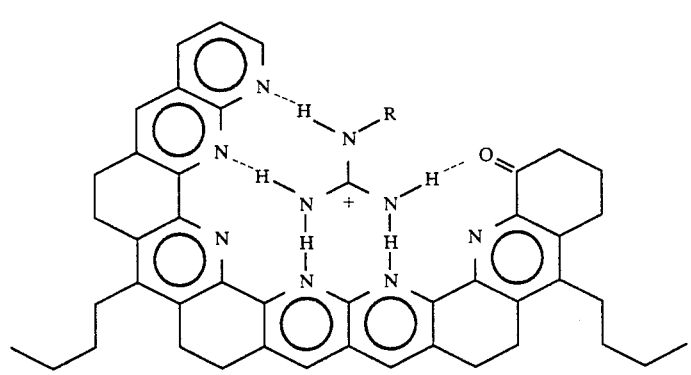
VIIIc
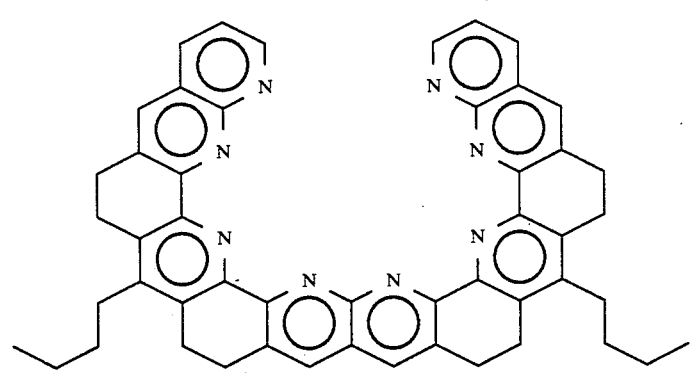
IX
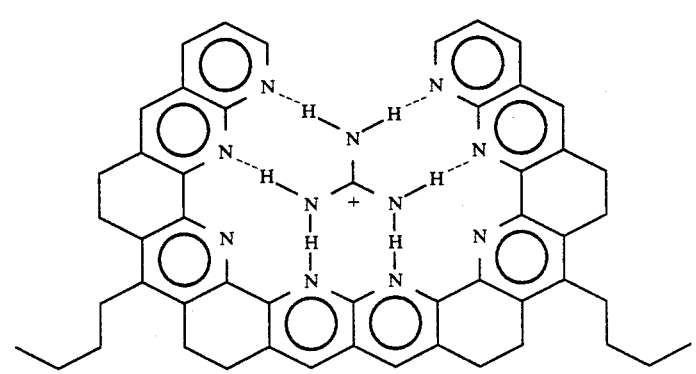
IXa

STRUCTURES -continued
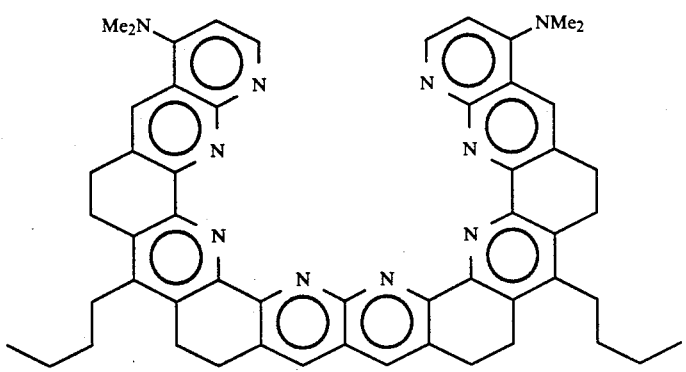
IXb
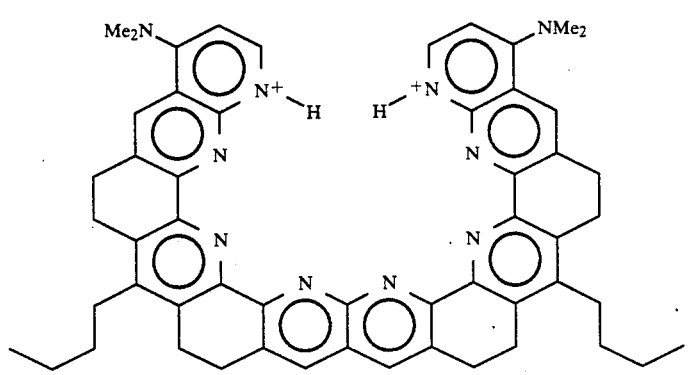
IXc
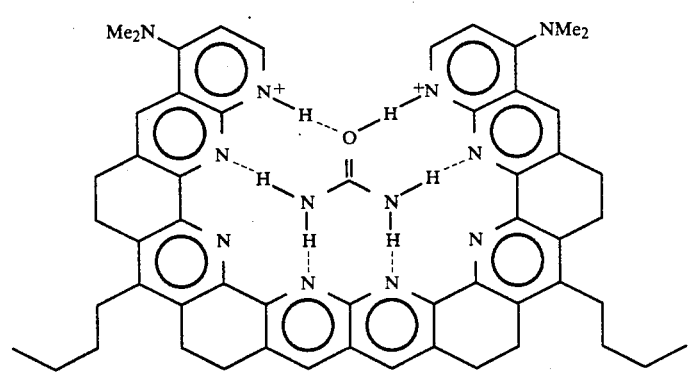
IXd
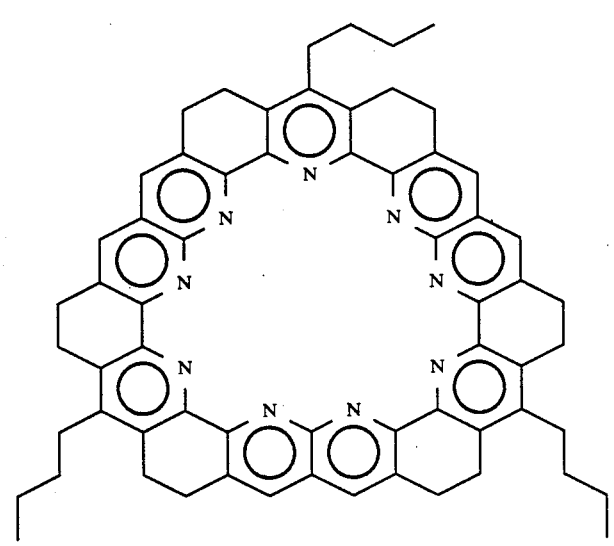
IXe -continued
STRUCTURES
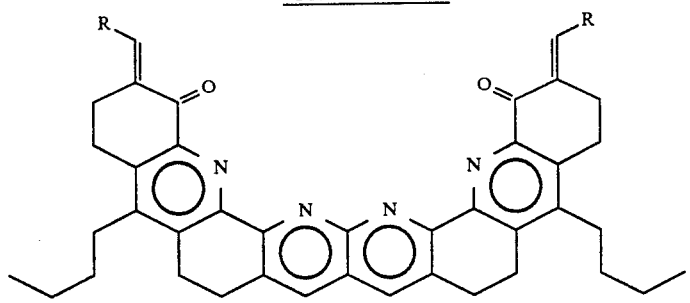
X R HC=CHNMe₂
XI R = 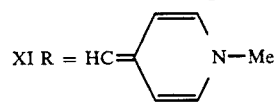
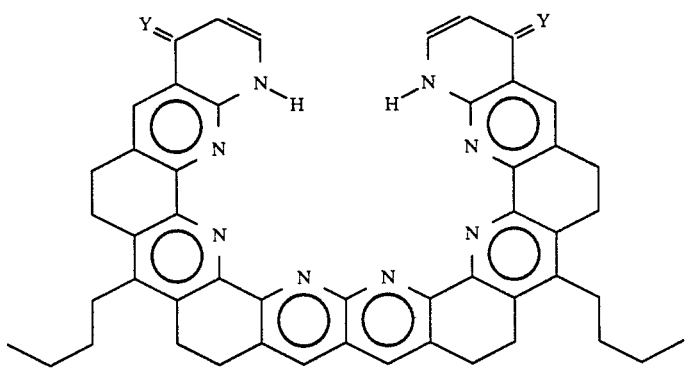
XII Y = O
XIII Y = C(CN)CO₂CH₃
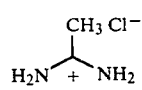 XIIIa
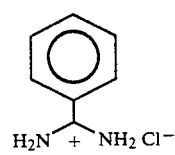 XIIIb
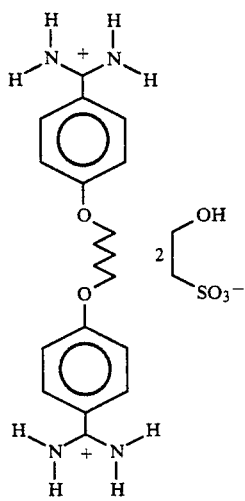 XIIIc REACTIONS
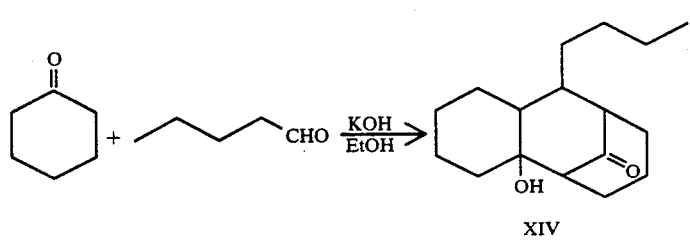 (1)
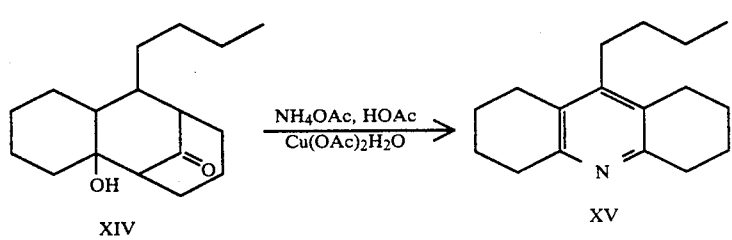 (2)
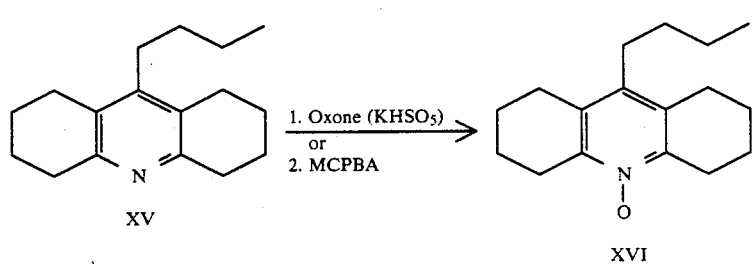 (3)
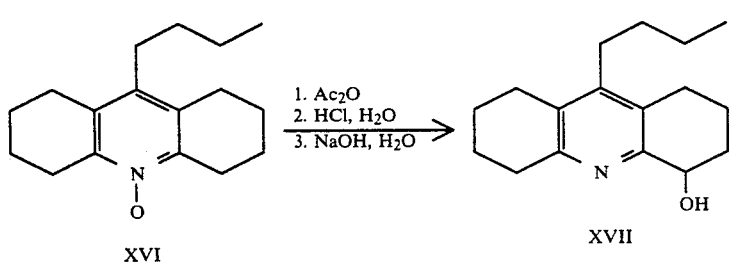 (4)
(5)
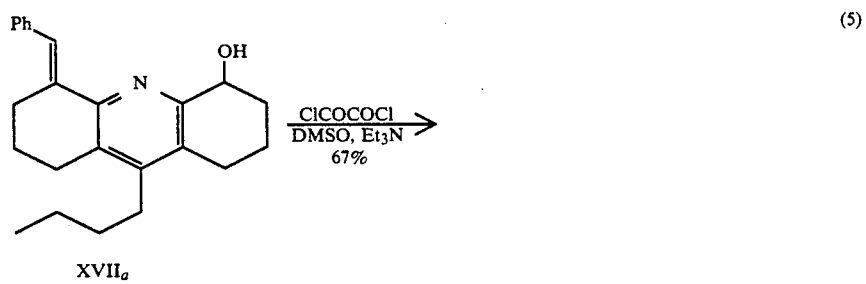
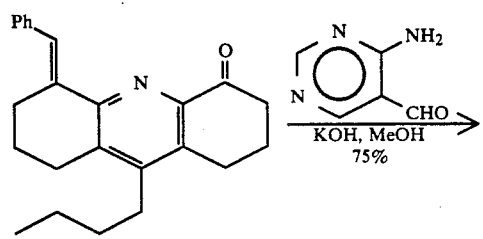

-continued
REACTIONS
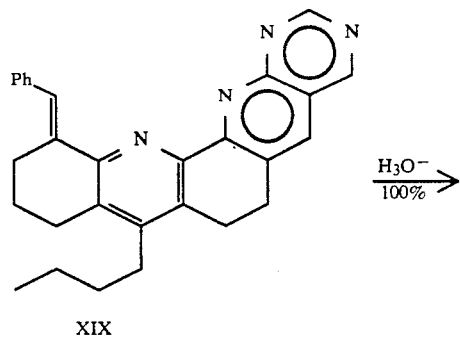
XIX
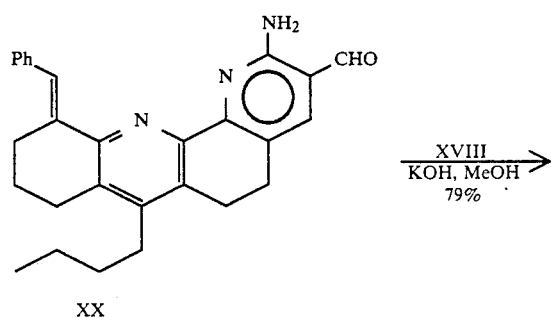
XX
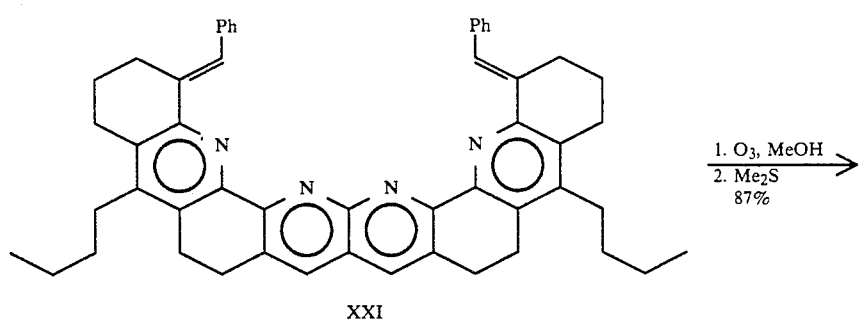
XXI
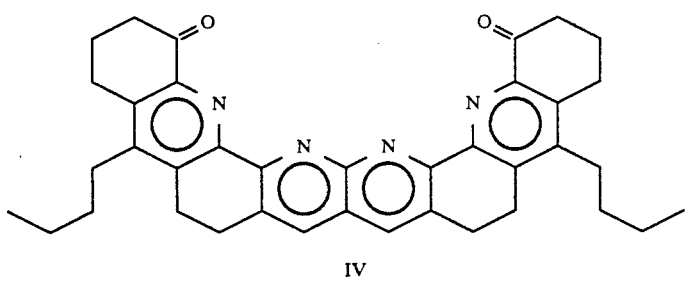
IV
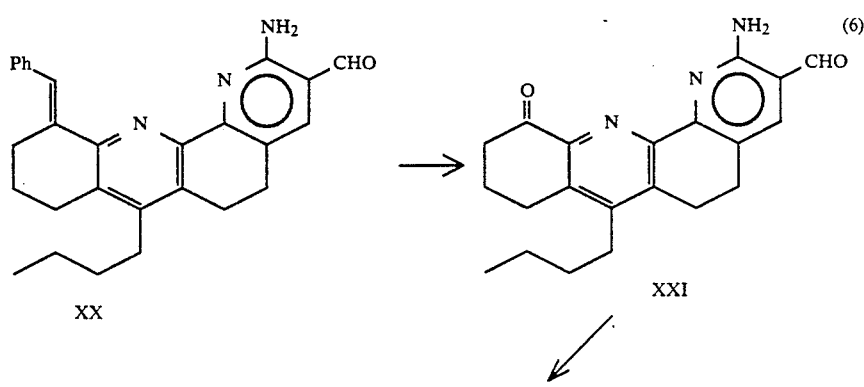
XX    XXI    (6)

REACTIONS
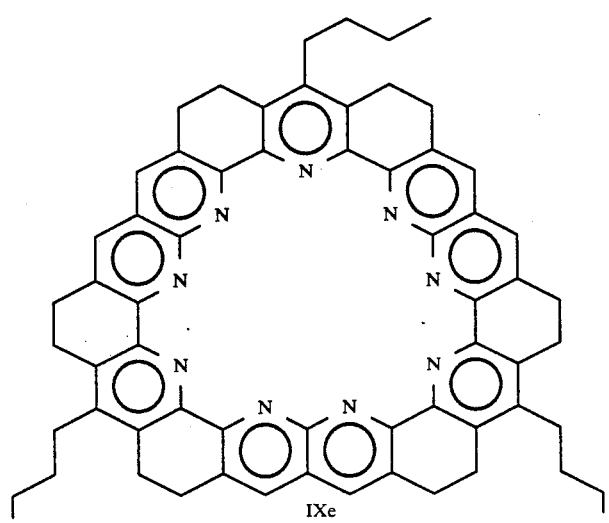
-continued
What is claimed is:
1. A molecule capable of forming stable complexes with urea, thiourea, guanidine, guanidine mono-substituted one nitrogen atom, guanidine di-substituted on one nitrogen atom, arginine or amidine compounds or an addition salt thereof comprising structures A'-G'.
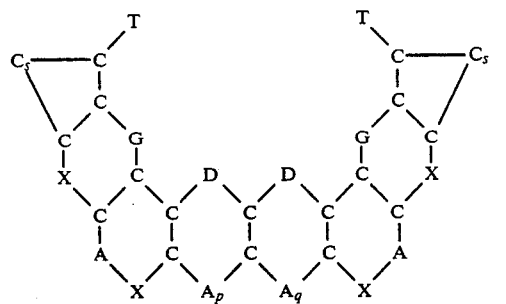
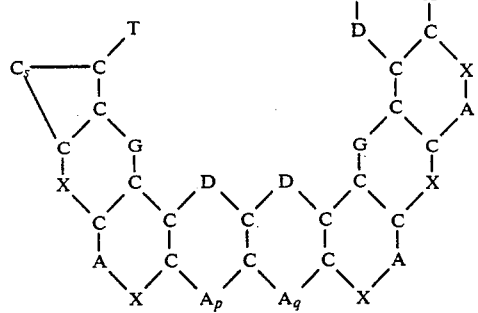
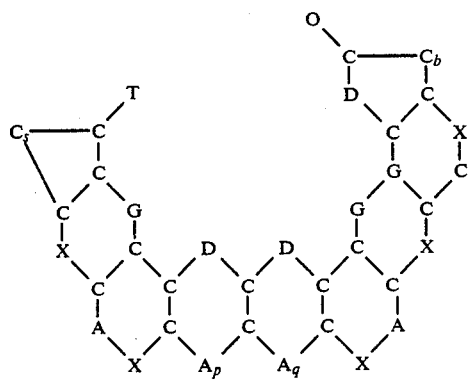
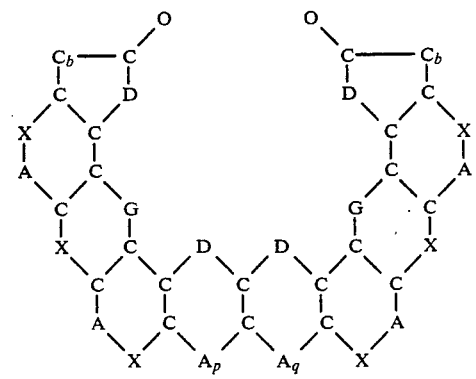

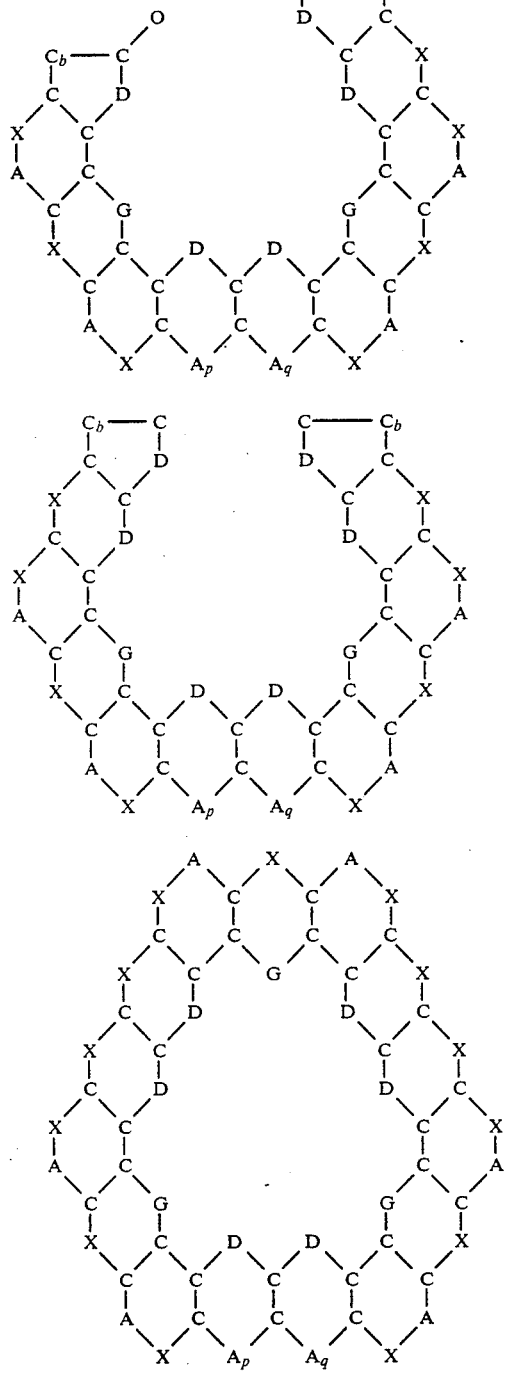

wherein:
C represents carbon atoms;
D independently represents nitrogen or oxygen atoms;
X independently represents $(A)_m$;
A and G independently represent carbon, sulfur, nitrogen or oxygen atoms;
O represents acyclic doubly bonded oxygen;
m=0–5;
b=0–6;
s=1–7;
p and q independently represent 0–2;

T independently represents nitrogen, oxygen or sulfur atoms;
wherein C, D, X, A, G and T atoms contain sufficient additional bonds to adjacent C, D, X, A, G or T atoms or to other atoms to lead to stable molecules; and
wherein an A or G atom that represents a sulfur, nitrogen or oxygen atom will not be adjacent to an A, G or T atom that also represents a sulfur, nitrogen or oxygen atom.

2. A molecule capable of forming stable complexes with urea, thiourea, guanidine, guanidine mono-substituted on one nitrogen atom, guanidine di-substituted on one nitrogen atom, arginine, an amidine compound or an addition salt thereof comprising structures A'' – G'':

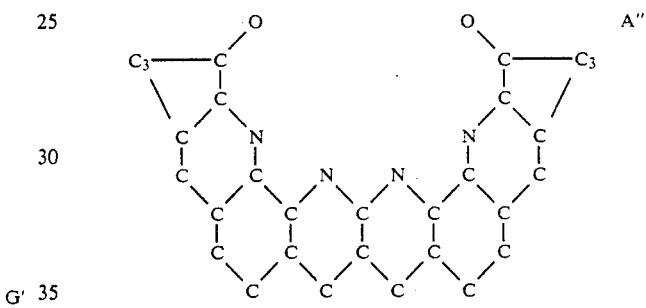

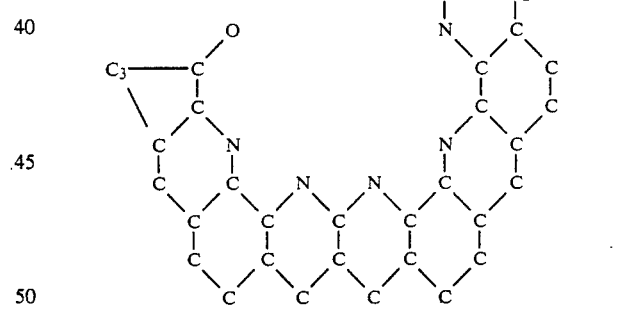

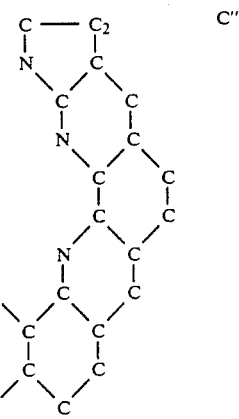

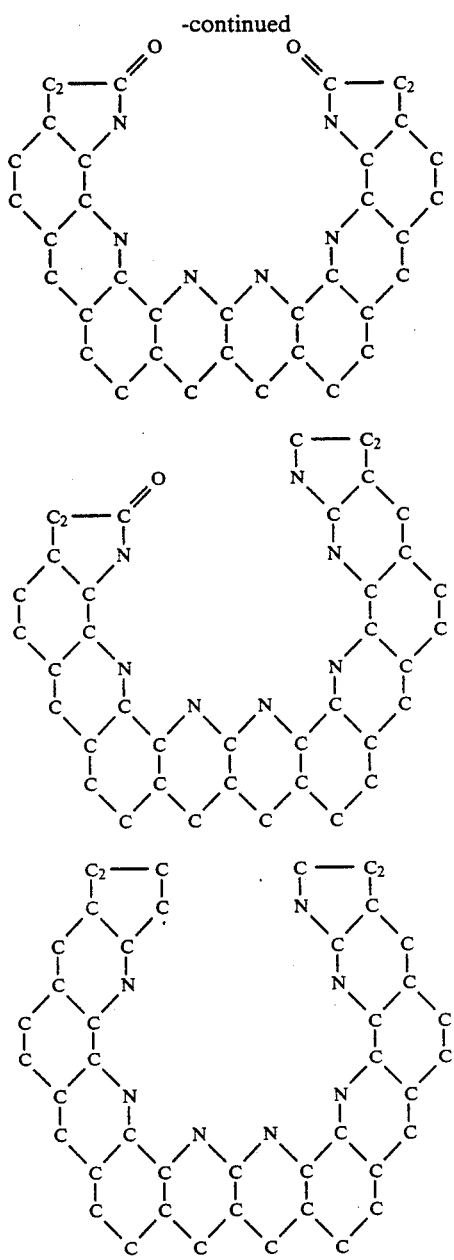

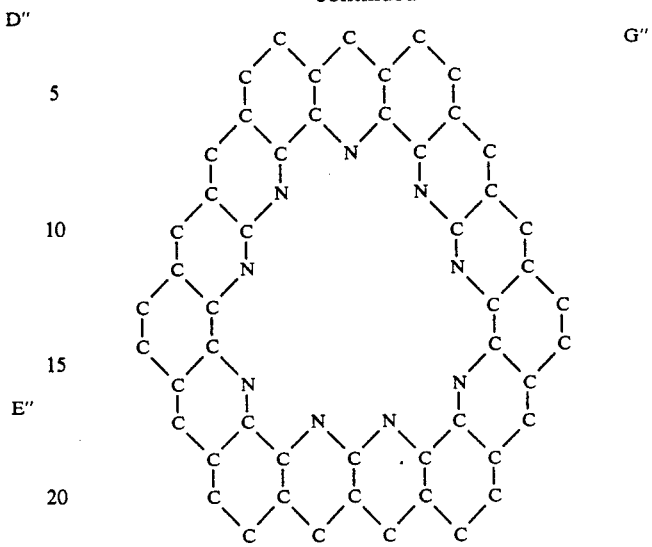

wherein
C represents carbon atoms;
N represents sp² hybridized nitrogen atoms;
—O represents sp² hybridized oxygen atoms; =O represents acyclic double bonded oxygen atoms;
wherein C, N and O atoms contain sufficient additional bonds to adjacent C, N, O atoms or to other atoms to lead to stable molecules.

3. A molecule according to claim 2 further comprising a chromophoric substituent that can be detected by spectroscopy, said chromophoric substituent having electrons conjugated with electrons on an atom that forms a hydrogen bond with the urea, guanidine or amidine compound.

4. A molecule capable of forming stable complexes with urea, guanidine or amidine compounds, comprising structure IV:

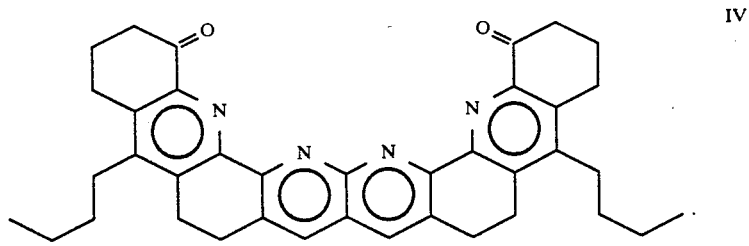

5. A molecule capable of forming stable complexes with urea, guanidine or amidine compounds, comprising structure V:

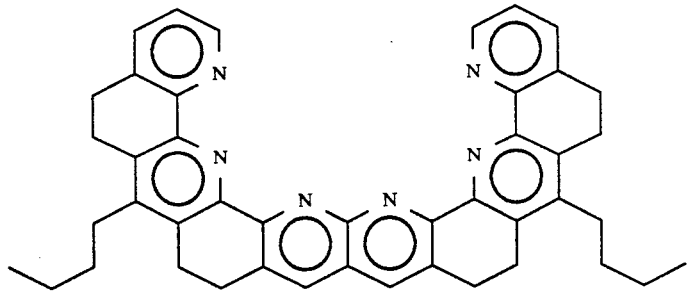

6. A molecule capable of forming stable complexes with urea, guanidine or amidine compounds comprising structure VI:

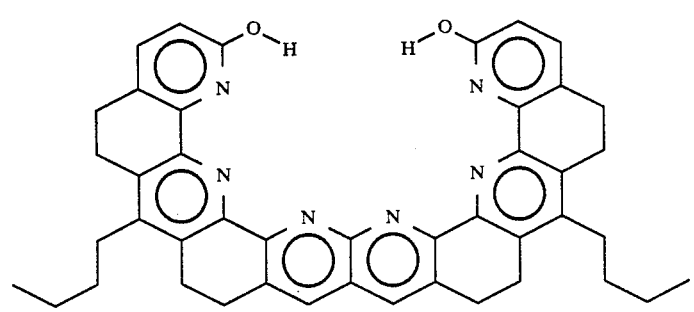

wherein D independently represents nitrogen, oxygen or sulfur atoms containing sufficient additional bonds to adjacent atoms or to other atoms to lead to stable molecules.

7. A molecule capable of forming stable complexes with urea, guanidine or amidine compounds comprising structure VII or VIII:

wherein
in structure VII, R—H, and
in structure VIII, R=COCH$_3$.

8. A molecule capable of forming stable complexes with urea, guanidine or amidine compounds comprising structure VIIIb:

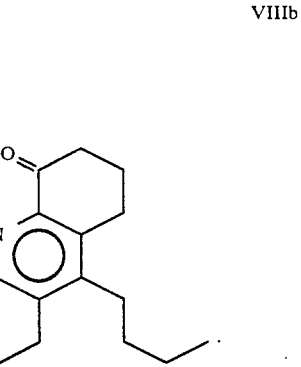

9. A molecule capable of forming stable complexes with urea, guanidine or amidine compounds comprising structure IX:

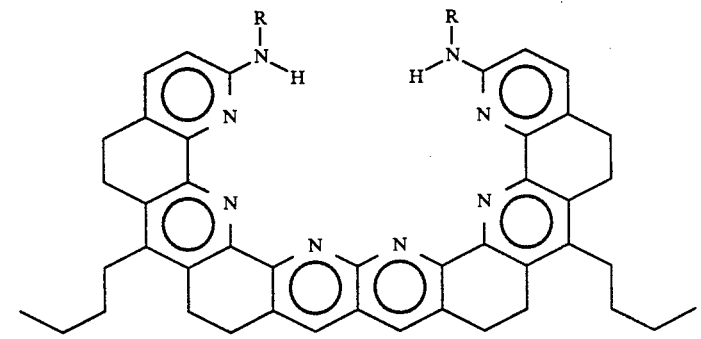

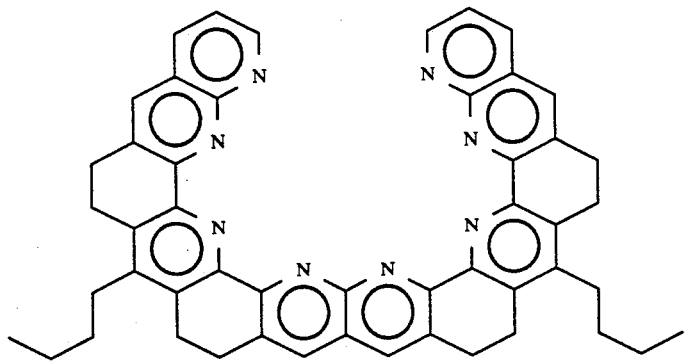
IX
10. A molecule capable of forming stable complexes with urea, guanidine or amidine compounds comprising structure IXe:
11. A molecule capable of forming stable complexes with urea, guanidine or amidine compounds comprising structure IXb or IXc:
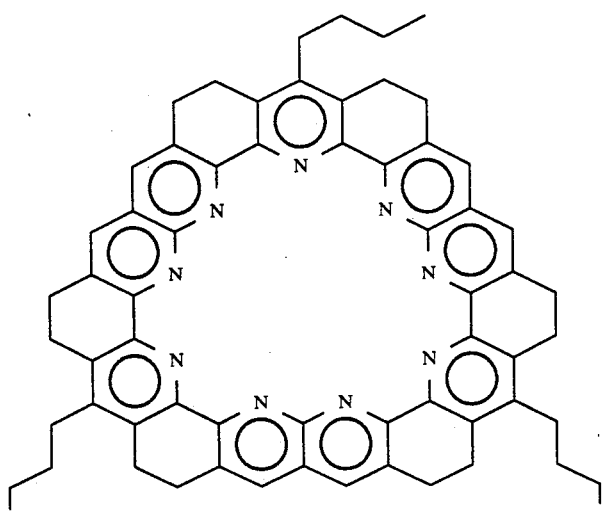
IXe
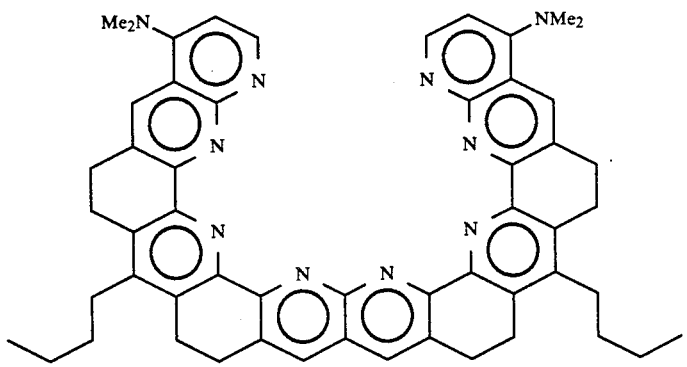
IXb -continued
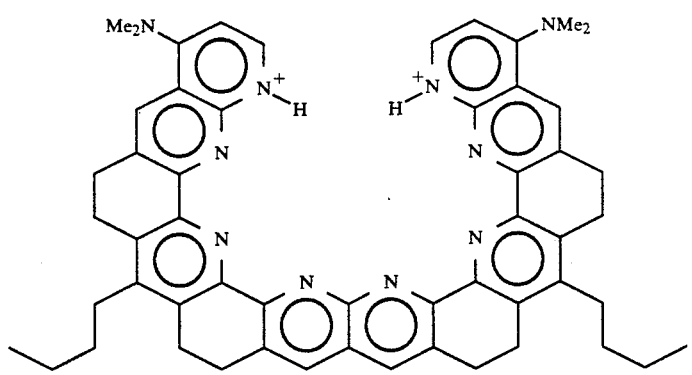
IXc
12. A molecule capable of forming stable complexes with urea, guanidine or amidine compounds comprising structures X, XI, XII or XIII:
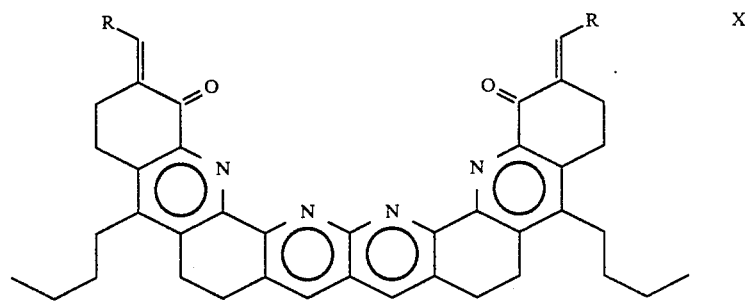
X
R = HC=CHNMe₂;
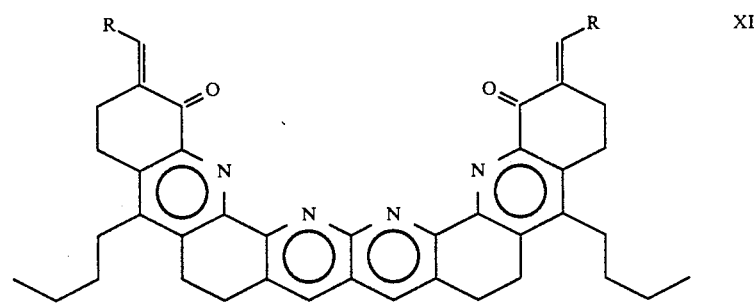
XI
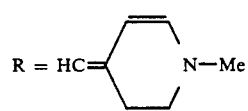
R = HC=
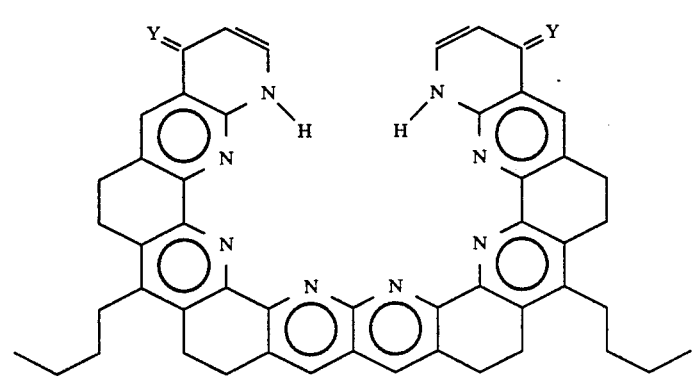
XII
Y = O;

XIII

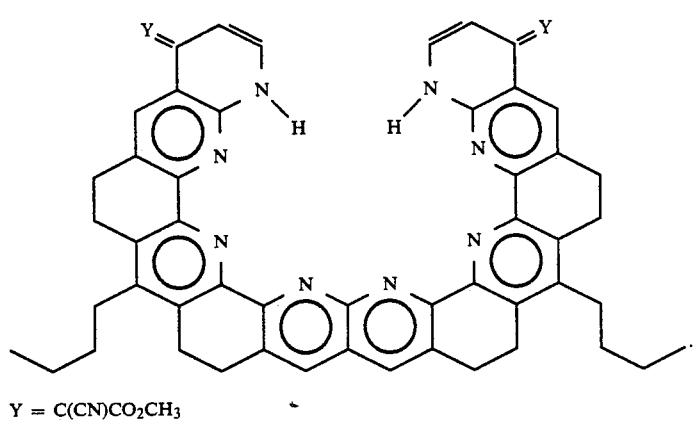

Y = C(CN)CO₂CH₃

13. A complex comprising a molecule of claim 2 complexed with a member of the group consisting of urea, thiourea, guanidine, guanidine mono-substituted on one nitrogen atom, guanidine di-substituted on one nitrogen atom, an amidine compound or an addition salt thereof.

14. A complex according to claim 13, wherein the substituted guanidine is N-methylguanidine, guanidoacetic acid, guanidopropionic acid, or quanidosuccinic acid.

15. A complex comprising structure IVa:

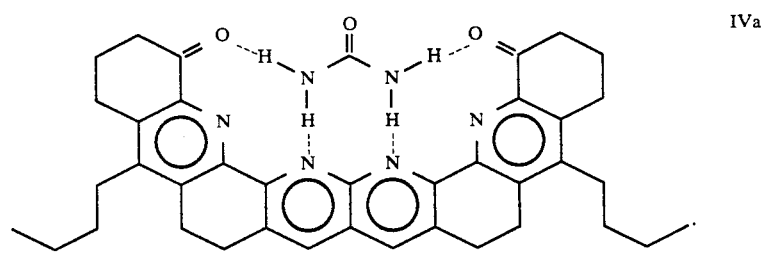

16. A complex comprising structure IVb:

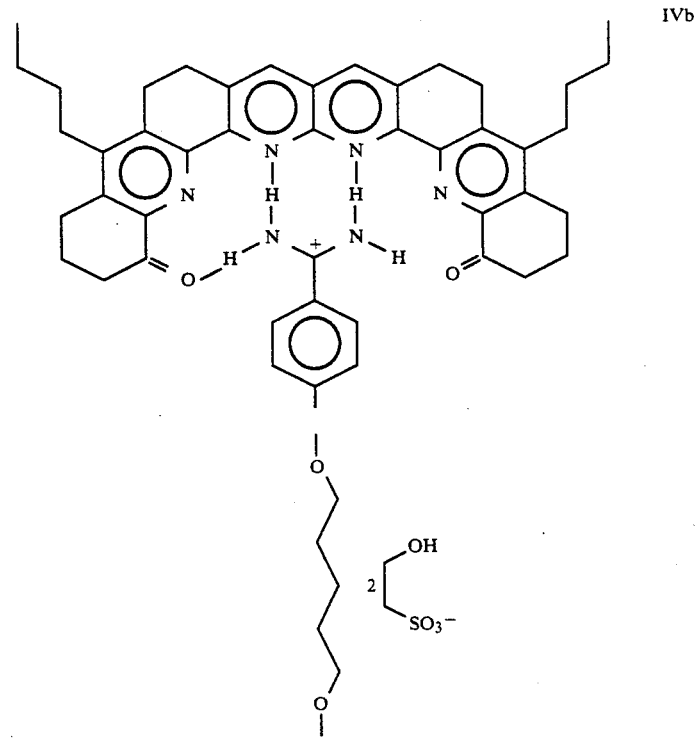

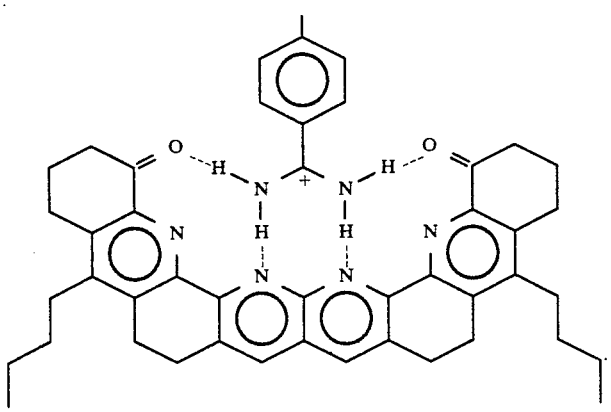

17. A complex comprising structure Va:

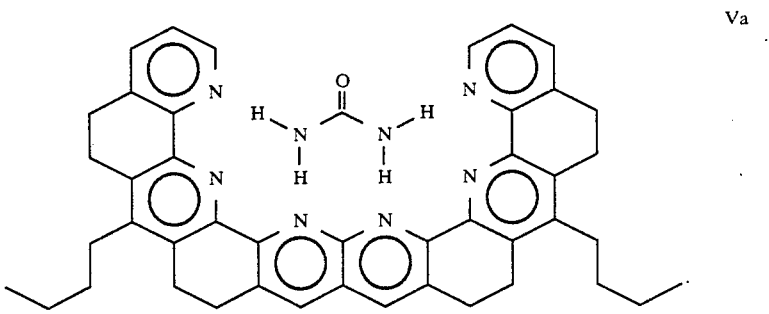

18. A complex comprising structure VIa:

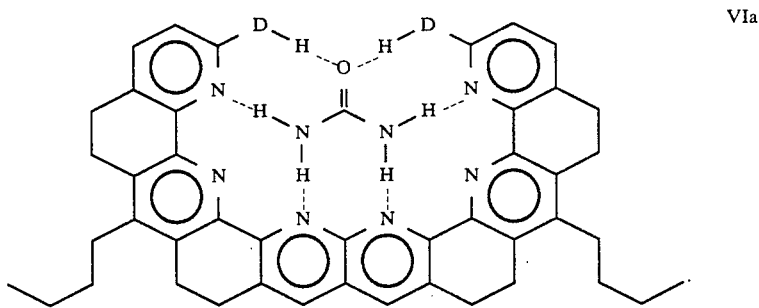

wherein D independently represents nitrogen, oxygen or sulfur atoms containing sufficient additional bonds to adjacent atoms or to other atoms to lead to stable molecules.

19. A complex comprising structure VIIa or VIIIa:

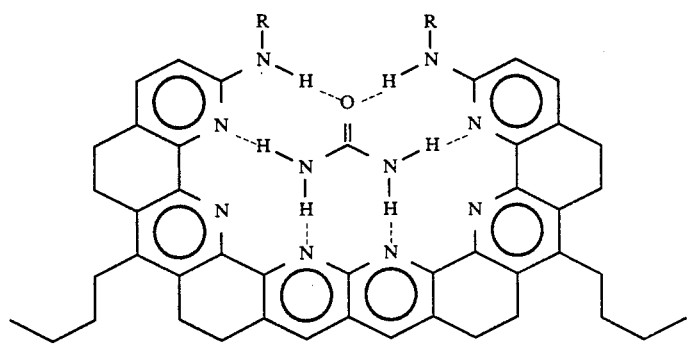

wherein in the complex of VIIa, R=H; and in the complex of VIIIa, R=COCH₃.

20. A complex comprising structure VIIIc:

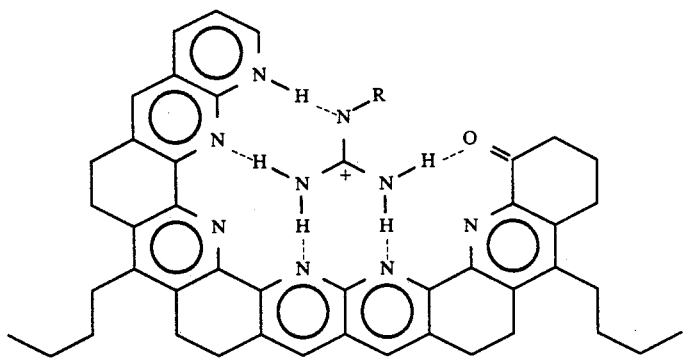
wherein R=H or an arginine residue.
21. A complex comprising structure IXa:
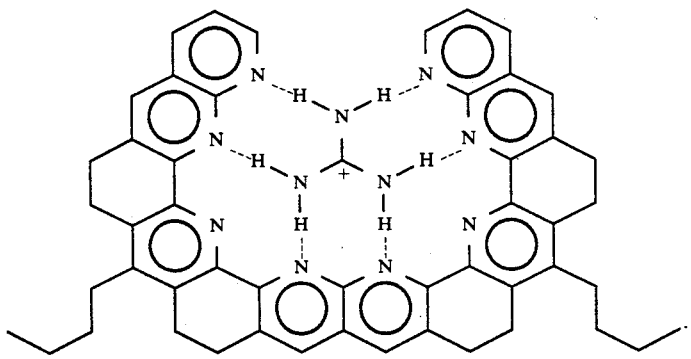
22. A complex comprising structure IXd:
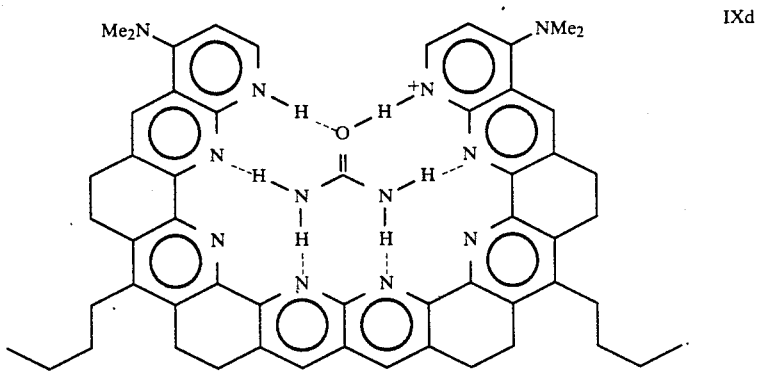
* * * * *

UNITED STATES PATENT AND TRADEMARK OFFICE
CERTIFICATE OF CORRECTION

PATENT NO. : 5,030,728
DATED : July 9, 1991
INVENTOR(S) : Bell

It is certified that error appears in the above-identified patent and that said Letters Patent is hereby corrected as shown below:

Column 1, line 5, insert

-- This invention was made with government support under grant number GM-32937 awarded by the National Institute of Health. The government has certain rights in the invention. --

Signed and Sealed this

Ninth Day of November, 1993

Attest:

BRUCE LEHMAN

Attesting Officer

Commissioner of Patents and Trademarks